US009312502B2

(12) United States Patent
Li et al.

(10) Patent No.: US 9,312,502 B2
(45) Date of Patent: Apr. 12, 2016

(54) IRIDIUM COMPLEXES DEMONSTRATING BROADBAND EMISSION THROUGH CONTROLLED GEOMETRIC DISTORTION AND APPLICATIONS THEREOF

(71) Applicants: Jian Li, Phoenix, AZ (US); Eric Turner, Chandler, AZ (US)

(72) Inventors: Jian Li, Phoenix, AZ (US); Eric Turner, Chandler, AZ (US)

(73) Assignee: Arizona Board of Regents acting for and on behalf of Arizona State University, Scottsdale, AZ (US)

( * ) Notice: Subject to any disclaimer, the term of this patent is extended or adjusted under 35 U.S.C. 154(b) by 113 days.

(21) Appl. No.: 13/963,519

(22) Filed: Aug. 9, 2013

(65) Prior Publication Data
US 2014/0073798 A1 Mar. 13, 2014

Related U.S. Application Data

(60) Provisional application No. 61/682,058, filed on Aug. 10, 2012.

(51) Int. Cl.
| | |
|---|---|
| *C07F 15/00* | (2006.01) |
| *H01L 51/00* | (2006.01) |
| *C09K 11/06* | (2006.01) |
| *H01L 51/42* | (2006.01) |
| *H01L 51/50* | (2006.01) |

(52) U.S. Cl.
CPC ........ *H01L 51/0085* (2013.01); *C07F 15/0033* (2013.01); *C09K 11/06* (2013.01); *C09K 2211/1029* (2013.01); *C09K 2211/1044* (2013.01); *C09K 2211/185* (2013.01); *H01L 51/42* (2013.01); *H01L 51/5016* (2013.01); *Y02E 10/549* (2013.01)

(58) Field of Classification Search
CPC .................................................. C07F 15/0033
See application file for complete search history.

(56) References Cited

U.S. PATENT DOCUMENTS

| 7,635,792 B1 | 12/2009 | Cella et al. |
| 8,133,597 B2 | 3/2012 | Yasukawa et al. |
| 2006/0127696 A1 | 6/2006 | Stossel et al. |
| 2006/0182992 A1 | 8/2006 | Nii et al. |
| 2006/0255721 A1 | 11/2006 | Igarashi et al. |
| 2008/0111476 A1 | 5/2008 | Choi et al. |
| 2010/0270540 A1 | 10/2010 | Chung et al. |
| 2011/0049496 A1 | 3/2011 | Fukuzaki |
| 2012/0264938 A1 | 10/2012 | Li et al. |

FOREIGN PATENT DOCUMENTS

| CN | 1680366 A | * 10/2005 | ........... C07D 401/04 |
| WO | 2008131932 | 6/2008 | |
| WO | 2010007098 | 1/2010 | |
| WO | 2010093176 | 8/2010 | |
| WO | 2011070989 | 6/2011 | |

OTHER PUBLICATIONS

Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.*
H Tang et al., "Novel yellow phosphorescent iridium complexes containing a carbazoleeoxadiazole unit used in polymeric light-emitting diodes", Dyes and Pigments 91 (2011) pp. 413-421.
D Wang et al., "Carbazole and arylamine functionalized iridium complexes for efficient electro-phosphorescent light-emitting diodes", Inorganica Chimica Acta 370 (2011) pp. 340-345.
JW Levell et al., "Carbazole/iridium dendrimer side-chain phosphorescent copolymers for efficient light emitting devices", New J. Chem., 2012, 36, pp. 407-413.
Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.
H-J Seo et al., "Blue phosphorescent iridium(III) complexes containing carbazole-functionalized phenylpyridine for organic light-emitting diodes: energy transfer from carbazolyl moieties to iridium(III) cores", RSC Advances, 2011, 1, pp. 755-757.
Z Xu et al., "Synthesis and properties of iridium complexes based 1,3,4-oxadiazoles derivatives", Tetrahedron 64 (2008) pp. 1860-1867.
C Ulbricht et al., "Synthesis and Characterization of Oxetane-Functionalized Phosphorescent Ir(III)-Complexes", Macromol. Chem. Phys. 2009, 210, pp. 531-541.

* cited by examiner

*Primary Examiner* — Joseph Kosack
(74) *Attorney, Agent, or Firm* — Ballard Spahr LLP

(57) ABSTRACT

Iridium compounds and their uses are disclosed herein. For example, carbazole containing iridium compounds are disclosed. The compounds are useful in many devices, including, but not limited to, electroluminescent devices.

4 Claims, 1 Drawing Sheet

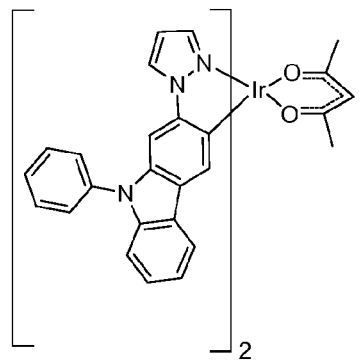
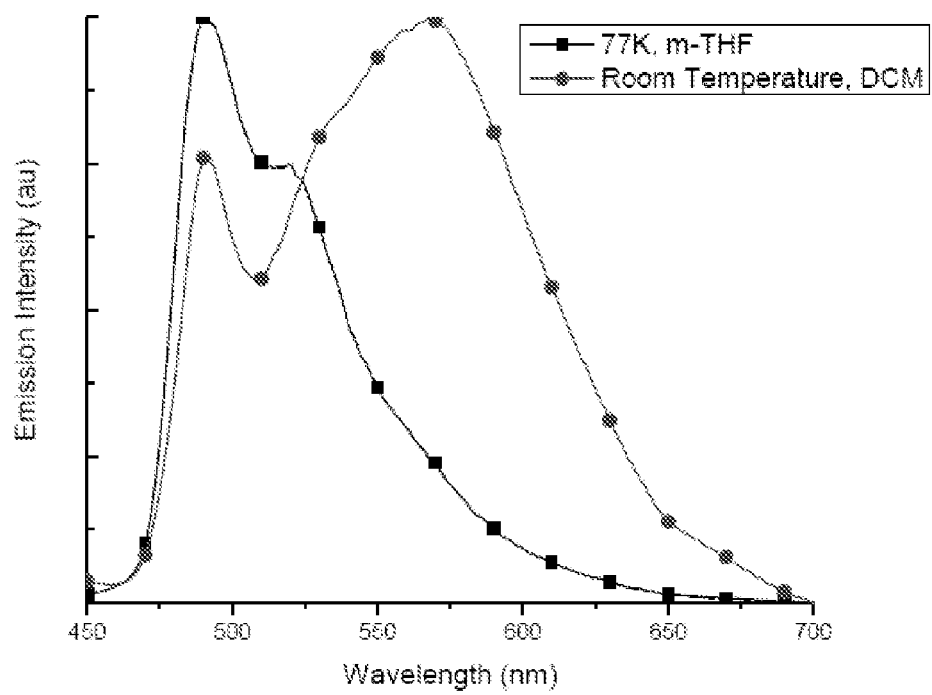

IRIDIUM COMPLEXES DEMONSTRATING BROADBAND EMISSION THROUGH CONTROLLED GEOMETRIC DISTORTION AND APPLICATIONS THEREOF

CROSS-REFERENCE TO RELATED APPLICATIONS

This Application claims the benefit of U.S. Provisional Application No. 61/682,058, filed on Aug. 10, 2012, which is incorporated herein by reference in its entirety.

STATEMENT OF GOVERNMENT SUPPORT

The present invention was made with financial support from the United States Department of Energy under Career Grant No. DOE DE-EE0005075. The U.S. government has certain rights in this invention.

TECHNICAL FIELD

The present disclosure relates to iridium complexes that can be useful in, for example, electroluminescent devices.

TECHNICAL BACKGROUND

Compounds capable of absorbing and/or emitting light are ideally suited for use in a wide variety of applications, including optical and electro-optical devices, photo-absorbing devices, and as markers for bio-applications. Much research has been devoted to the discovery and optimization of organic and organometallic materials for use in such applications. Generally, research in this area aims to accomplish a number of goals, including improvements in absorption and emission efficiency, as well as improvements in processing ability, among others.

Despite significant advances in research devoted to optical, electro-optical, and marker materials, existing materials have a number disadvantages, including poor processing ability, inefficient emission or absorption, and less than ideal stability, among others. Thus, a need exists for new materials which exhibit improved performance in optical emitting and absorbing applications. This need and other needs are satisfied by the present invention.

SUMMARY

The disclosure herein relates to iridium complexes that can be useful in devices, such as electroluminescent devices, including, but not limited to, narrow band phosphorescent emitters in, for example, full color displays. Such complexes are useful in organic-light-emitting-diodes (OLEDs).

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. An "exciton," which is a localized electron-hole pair having an excited energy state, is formed when an electron and hole localize on the same molecule. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

In one aspect, the compounds disclosed herein can be represented by the general formula:

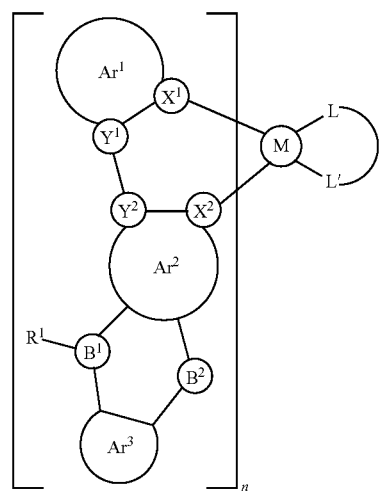

wherein:

M is iridium; wherein $Ar^1$ is aryl, cycloalkyl, or heterocyclic; wherein $Ar^2$ is aryl, cycloalkyl, or heterocyclic; wherein $Ar^3$ is aryl, cycloalkyl, or heterocyclic; wherein $X^1$ comprises a carbon or nitrogen atom and is coordinated to the iridium; wherein $X^2$ comprises a carbon or nitrogen atom and is coordinated to the iridium; wherein $Y^1$ comprises a carbon or nitrogen atom; wherein $Y^2$ comprises a carbon or nitrogen atom; wherein $B^1$ comprises an oxygen, sulfur, nitrogen, carbon, boron, phosphorus, or silicon atom; wherein the bond between $Ar^2$ and $Ar^3$ via $B^2$ is present or absent, when present $B^2$ is present or absent, and if present comprises an oxygen, sulfur, nitrogen, carbon, boron, phosphorus, or silicon atom; wherein $R^1$ is absent when $B^1$ is an oxygen or sulfur atom, and $R^1$ is present when $B^1$ is a nitrogen, carbon, boron, phosphorus, or silicon atom, and if present $R^1$ is selected from the group consisting of H, alkyl, aryl, cycloalkyl, heterocyclic, $-OR^2$, $C(O)OR^3$, $C(O)R^4$, wherein $R^2$, $R^3$, and $R^4$ are independently selected from H, alkyl, aryl, heterocyclic, and cycloalkyl; wherein L^L' represents a ligand.

In one aspect, the ligand is an ancillary portion of the complex and comprises

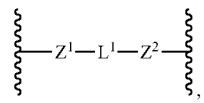

wherein $Z^1$ and $Z^2$ are independently selected from —O— and —S— and $L^1$ is selected from substituted or unsubstituted C1-C12 alkyl, C1-C12 alkenyl, and C1-C12 alkynyl; and wherein n is 1 or 2.

In another aspect, the ligands disclosed herein are emitting ligands, such as emitting fragments disclosed herein.

Also disclosed are electroluminescent devices, such as full color display devices, comprising one or more of the compounds (i.e. iridium complexes) disclosed herein.

BRIEF DESCRIPTION OF THE FIGURES

The accompanying figures, which are incorporated in and constitute a part of this specification, illustrate several aspects and together with the description serve to explain the principles of the invention.

FIG. 1 illustrates an emission spectra of the compound shown in the FIGURE and shows the room temperature spectra in degassed dichloromethane, and the 77K spectra in 2-methyltetrahyrdofuran, in accordance with various aspects of the present disclosure.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

The term "compound" and "complex" and the like terms are used interchangeably herein.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

The term "heterocyclic" or the like terms refer to cyclic structures including a heteroatom. Thus, "heterocyclic" includes both aromatic and non-aromatic ring structures with one or more heteroatoms. Non-limiting examples of heterocyclic includes, pyridine, isoquinoline, methylpyrrole and thiophene etc.

The term "cycloalkyl" or the like terms refer to a ring structure which is not aromatic and is free from heteroatoms in the core structure of the ring. Thus, a cycloalkyl includes ring structures with doubled bonds but which are not aromatic. Heteroatoms can be present as substituents from the ring structure. For example, a non limiting example of cycloalkyl is substituted and unsubstituted cyclohexane.

As briefly described above, the present invention is directed to compounds, such as iridium complexes. In one aspect, the compounds disclosed here can provide emission spectra of iridium. In another aspect, the compounds disclosed herein can provide tunable emission spectra. In yet another aspect, the compounds disclosed herein can have an emission spectrum having a narrow bandwidth.

In one aspect, the inventive composition comprises an iridium (III) complex. In one aspect, the invention comprises a tetradentate iridium (III) complex. In another aspect, the invention comprises a hexadentate iridium (III) complex. In another aspect, the inventive composition comprises an iridium (IV) complex.

In one aspect, reference to a "C" or an "N" as used herein refers to a moiety comprising a carbon or nitrogen atom, respectively.

For any of the structures recited herein, unless specifically stated to the contrary, various symbols and/or abbreviations are used wherein: M represents iridium, where each of $Ar^1$, $Ar^2$, and $Ar^3$, if present, independently represent an aromatic ring, cycloalkyl or heterocyclic group which can be substituted or unsubstituted; where each $X^n$ can be coordinated to a iridium atom, and can independently represent a carbon and/or a nitrogen atom, wherein each $Y^n$ can independently represent a carbon and/or a nitrogen atom, wherein $B^1$ is a linking atom, such as, for example, nitrogen, oxygen carbon, boron, phosphorus, silicon, or a combination thereof, and wherein each $B^1$ can optionally be substituted, wherein $B^2$ can optionally be present or absent, and if present can independently represent oxygen, sulfur, nitrogen, carbon, boron, phosphorus, silicon, or a combination thereof.

Also, for any of the structures recited herein, $R^n$ can represent $R^1$-$R^{10}$, where each R can independently represent a hydrogen atom, an alkyl group, a haloalkyl group, an aralkyl group, an alkenyl group, an alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, amercapto group, a halogen atom, a cyano group, a sulfo group, a carboxyl group, a nitro group, a hydrzino group, a substituted silyl group, a polymerizable group, or a combination thereof; wherein if a plurality of R's are present (e.g., $R_n$), n can be from about 0 to about 4, and wherein each R can be the same or different from any other R, and wherein U, if present, can be oxygen, sulfur, or N—$R_n$. Also, designation of $R^1$, $R^2$, and $R^3$ etc in the application relates to the definition of R. Thus, limited subset of $R^1$, $R^2$, and $R^3$ etc recited in the application does not preclude other substituents defined as $R_n$ to also be included in that list.

In one aspect, the compounds disclosed herein can be represented by the general formula:

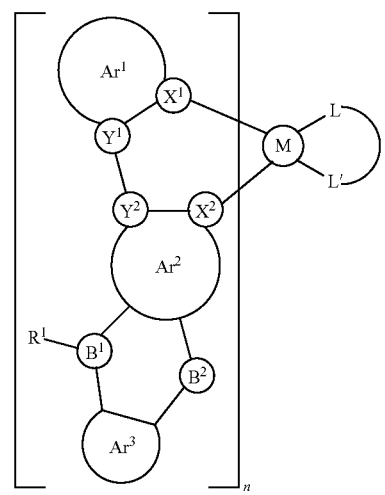

wherein:

M is iridium; wherein $Ar^1$ is aryl, cycloalkyl, or heterocyclic; wherein $Ar^2$ is aryl, cycloalkyl, or heterocyclic; wherein $Ar^3$ is aryl, cycloalkyl, or heterocyclic; wherein $X^1$ comprises a carbon or nitrogen atom and is coordinated to the iridium; wherein $X^2$ comprises a carbon or nitrogen atom and is coordinated to the iridium; wherein $Y^1$ comprises a carbon or nitrogen atom; wherein $Y^2$ comprises a carbon or nitrogen atom; wherein $B^1$ is selected from an oxygen, sulfur, nitrogen, carbon, boron, phosphorus, and silicon atom; wherein the bond between $Ar^2$ and $Ar^3$ via $B^2$ is present or absent, and if present $B^2$ is present or absent, and if present comprises an oxygen, sulfur, nitrogen, carbon, boron, phosphorus, or silicon atom; wherein $R^1$ is absent when $B^1$ is an oxygen or sulfur atom, and $R^1$ is present when $B^1$ is a nitrogen, carbon, boron, phosphorus, or silicon atom, and if present $R^1$ is selected from the group consisting of H, alkyl, aryl, cycloalkyl, heterocyclic, —$OR^2$, $C(O)OR^3$, $C(O)R^4$, wherein $R^2$, $R^3$ and $R^4$ are independently selected from H, alkyl, aryl, heterocyclic, and cycloalkyl; wherein -L^L-' represents a ligand.

In one aspect, the ligand is an ancillary portion of the complex and comprises

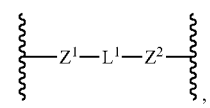

wherein $Z^1$ and $Z^2$ are independently selected from —O— and —S— and $L^1$ is selected from substituted or unsubstituted C1-C12 alkyl, C1-C12 alkenyl, and C1-C12 alkynyl; and wherein n is 1 or 2. In one aspect, n is 2.

In another aspect, a ligand is an emitting ligand, such as emitting fragments disclosed herein.

In another aspect, the compounds disclosed herein can be represented by the general formula:

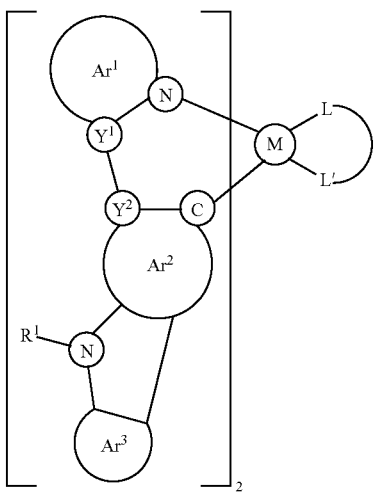
In another aspect, the compounds disclosed herein can be represented by the general formula:
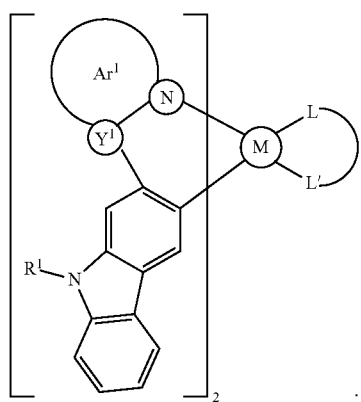
In another aspect, the compounds disclosed herein can be represented by the general formula:
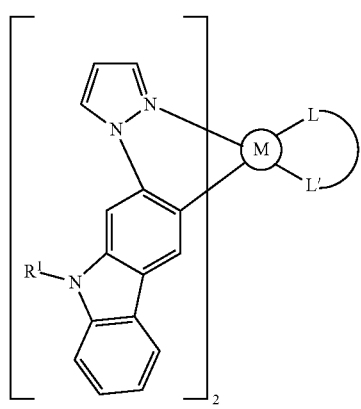
In one aspect, the formulas disclosed herein can comprise
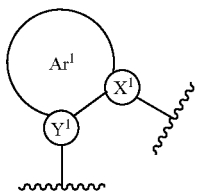
and can be selected from the group consisting of:
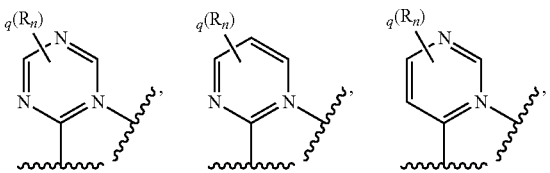
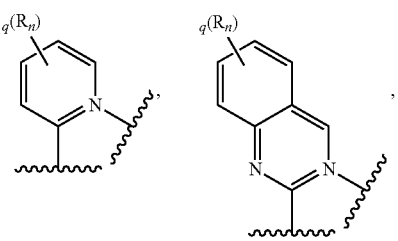
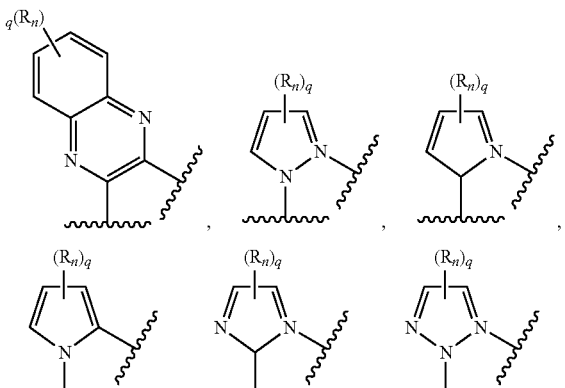
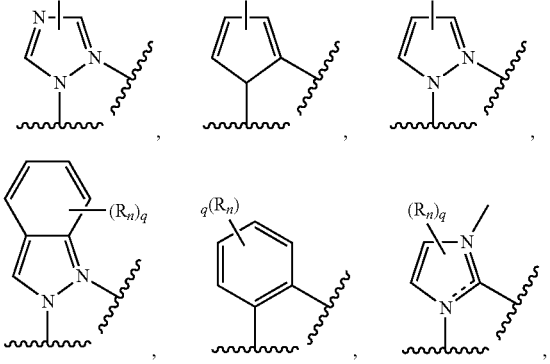

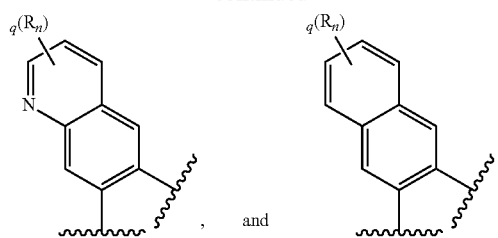
, and .

In one aspect, $R_n$ can be H or $C_1$-$C_3$ alkyl. In one aspect, q can be 1 or 0. For example, q can be 0. For example,

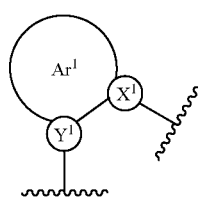

can be

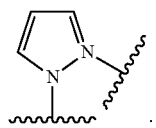

.

In one aspect, the formulas disclosed herein can comprise

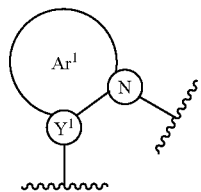

and can be selected from the group consisting of:

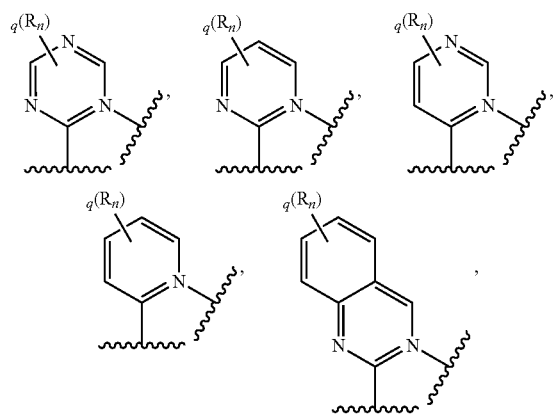

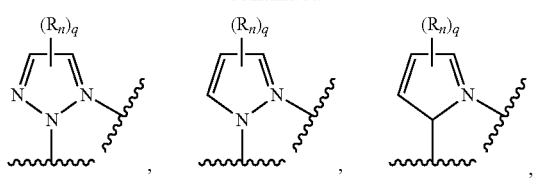

, , ,

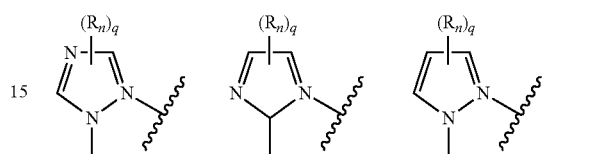

, , and

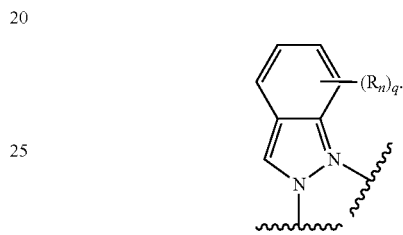

.

In one aspect, $R_n$ can be H or $C_1$-$C_3$ alkyl. In one aspect, q can be 1 or 0. For example, q can be 0. For example,

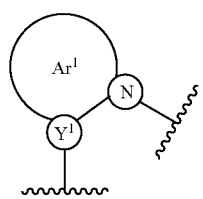

can be

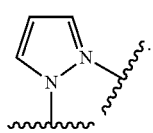

.

In one aspect, the formulas disclosed herein can comprise

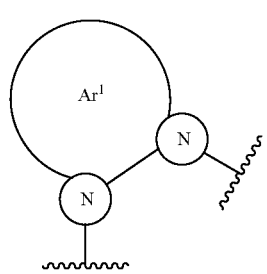

and can be selected from the group consisting of:
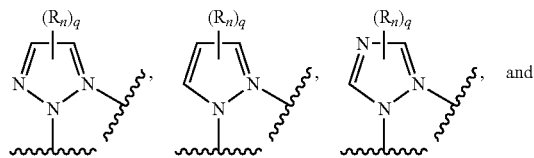
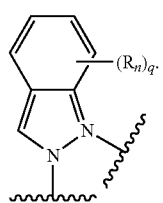
In one aspect, $R_n$ can be H or $C_1$-$C_3$ alkyl. In one aspect, q can be 1 or 0. For example, q can be 0.
In one aspect,
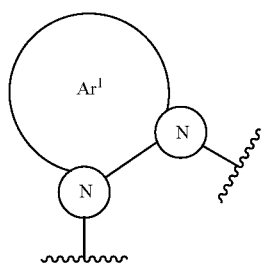
can be
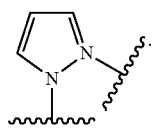
In one aspect, the formulas disclosed herein can comprise
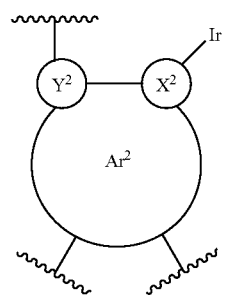
and can be selected from the group consisting of:
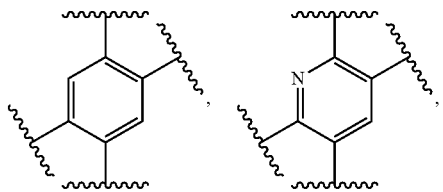
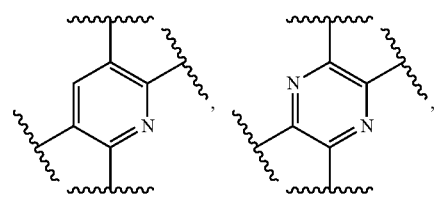
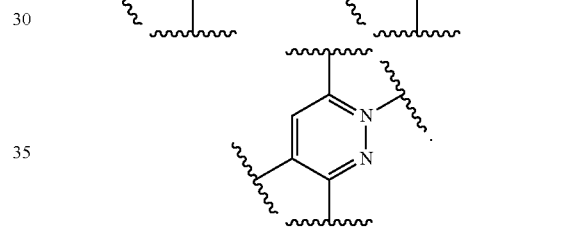
For example,
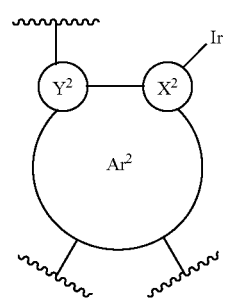
can be
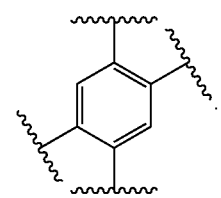 [SMILES: *c1cc(*)c(*)cc1*]

In one aspect, the formulas disclosed herein can comprise
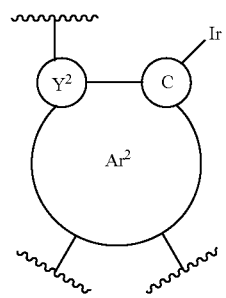
and can be selected from the group consisting of:
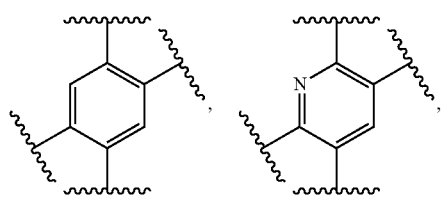
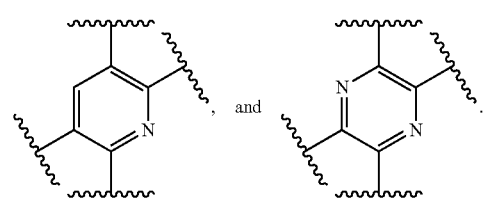
For example,
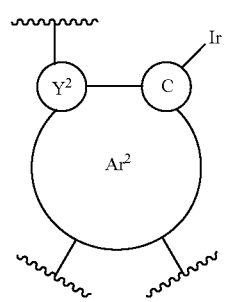
can be
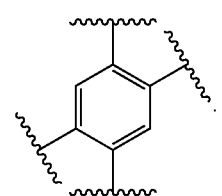 [SMILES: *c1cc(*)c(*)cc1*]
In one aspect, the formulas disclosed herein can comprise
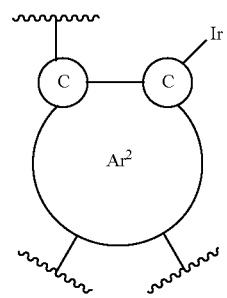
and can be selected from the group consisting of:
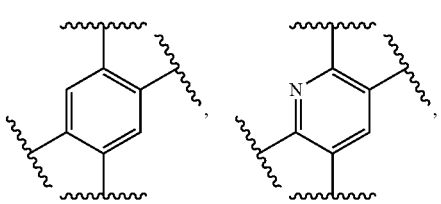
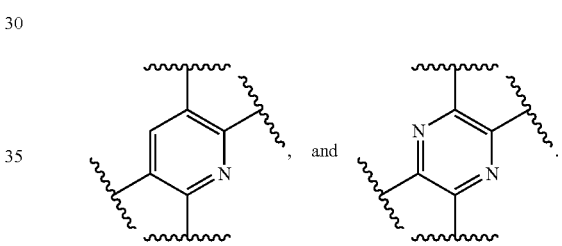
For example,
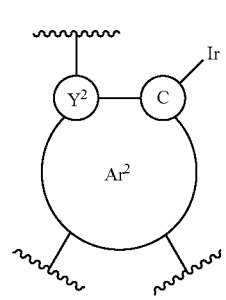
can be
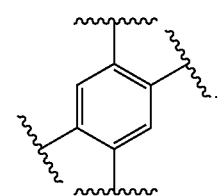 [SMILES: *c1cc(*)c(*)cc1*]

In another aspect, the formulas disclosed herein can comprise

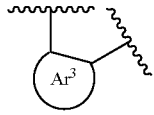

and can be selected from the group consisting of:

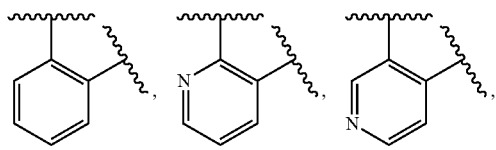

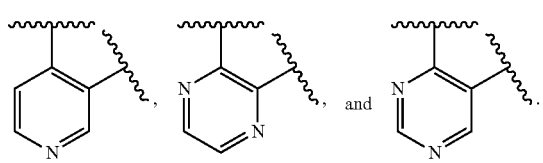

For example,

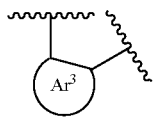

can be

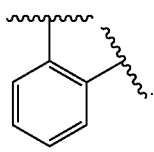 [SMILES: *c1ccccc1*]

In another aspect, in all formulas described herein,

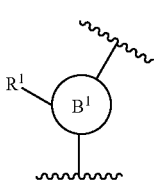

can comprise at least one oxygen atom, sulfur atom, nitrogen atom, carbon, boron, phosphorus, or silicon atom. For example,

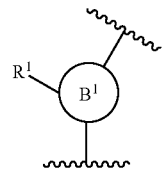

can comprise a nitrogen atom. In one aspect, $R^1$ is optionally present, for example,

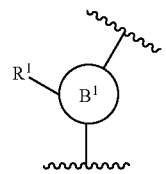

can be

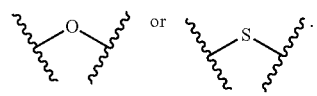

In another example,

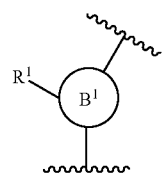

can be selected from the group consisting of:

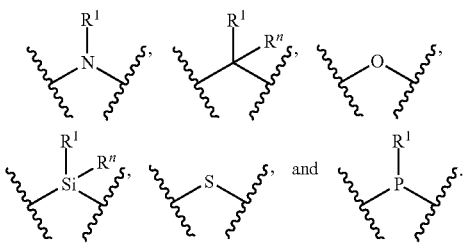

In one aspect, $R''$ can be H or $C_1$-$C_3$ alkyl. For example,

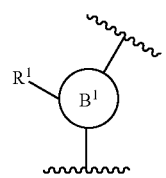

can be
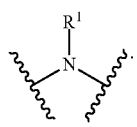
In one aspect,
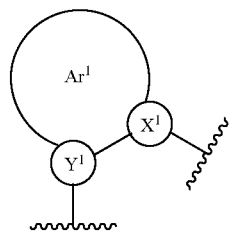
can be
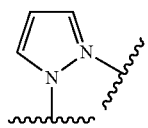
and
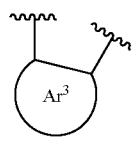
can be
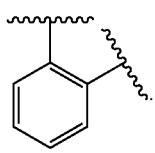
In one aspect,
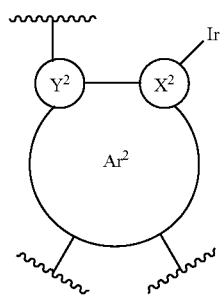
can be
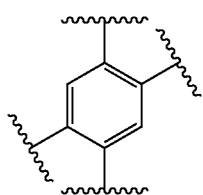 [SMILES: *c1cc(*)c(*)cc1*]
and
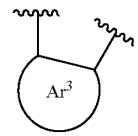
can be
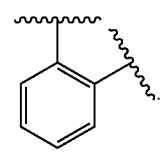
In one aspect,
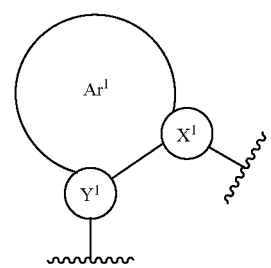
can be
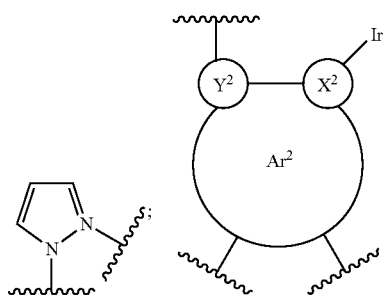

can be

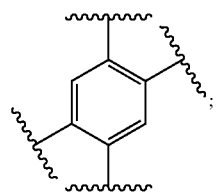

and

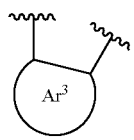

can be

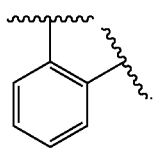

In one aspect,

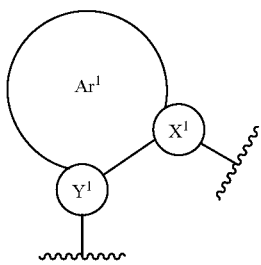

can be

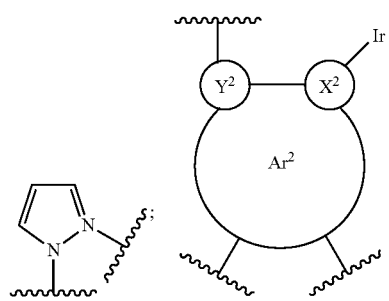

can be

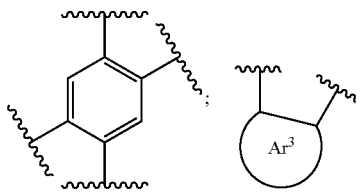

can be

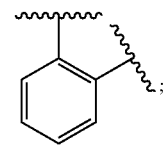 [SMILES: *c1ccccc1*]

and

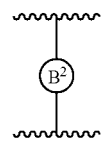

is absent.

In one aspect, the bond between $Ar^2$ and $Ar^3$ via $B^2$ is present or absent. In one aspect, the bond is absent. Thus, in such case there is no bond at all in such location. When the bond is present, in one aspect, in all formulas described herein,

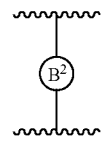

can be absent. Thus, $B^2$ is absent but there is a bond between $Ar^2$ and $Ar^3$ at such location. In another aspect, in all formulas described herein,

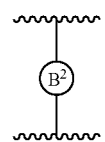

can be present. For example,

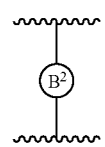

comprise at least one oxygen, sulfur, nitrogen, carbon, boron, phosphorus, or silicon atom. For example,

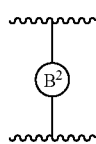

can be selected from

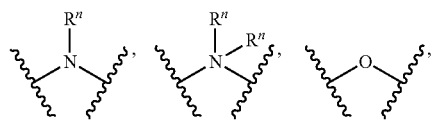

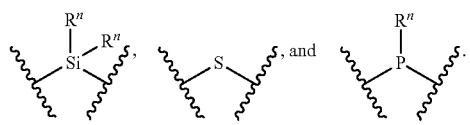

Each $R''$ can independently be H or or $C_1$-$C_3$ alkyl.

In another aspect, in all formulas described herein, $R^1$ when present can be selected from H, alkyl, aryl, cycloalkyl, heterocyclic, —$OR^2$, $C(O)OR^3$, and $C(O)R^4$, wherein $R^2$, $R^3$ and $R^4$ can independently selected from H, alkyl, aryl, heterocyclic, and cycloalkyl. For example, $R^1$ can be aryl, such as

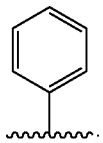

In one aspect,

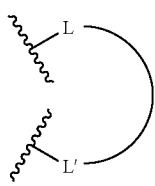

and L^L' are used interchangeably herein. In one aspect, in all formulas described herein, L^L' represents a ligand. For example, the ligand can be an ancillary portion of the complex. In one aspect, L^L' can comprise

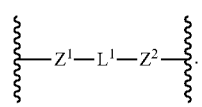

In one aspect, $Z^1$ and $Z^2$ are independently selected from —O— and —S—. For example $Z^1$ and $Z^2$ can be identical, such as that $Z^1$ and $Z^2$ are both —O—. $L^1$ can be selected from substituted or unsubstituted C1-C12 alkyl, C1-C12 alkenyl, and C1-C12 alkynyl. For example, $L^1$ can be substituted C1-C12 alkyl, C1-C12 alkenyl, and C1-C12 alkynyl. For example, $L^1$ can be

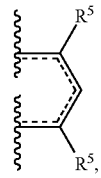

wherein $R^5$ is C1-C3 alkyl. In one non-limiting example,

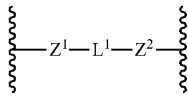

can be

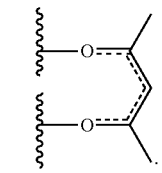

In one aspect,

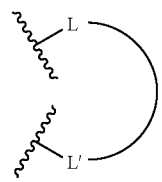

or L^L' is not an ancillary portion but an emitting fragment, such as those disclosed herein. Thus,

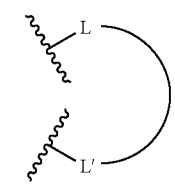

or L^L' can also be represented by

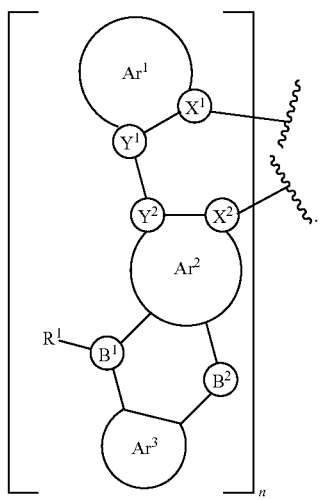

In other aspects, the disclosed compound is:

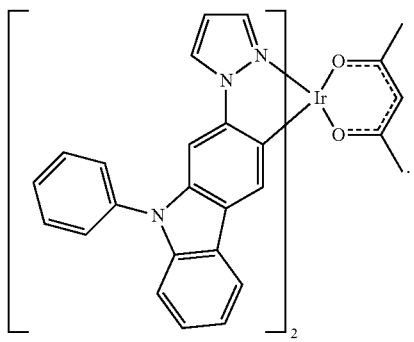

It should be understood that the specific exemplary compositions recited herein are intended to be exemplary and not limiting. In another aspect, the present invention can exclude, or not include, any one or more of the compounds recited herein In another aspect, the disclosed complexes can be a present in a composition as described herein.

The inventive compositions of the present disclosure can be useful in a wide variety of applications, such as, for example, lighting devices. In a particular aspect, one or more of the complexes can be useful as an emitter for an organic light emitting display device.

The compounds of the invention are useful in a variety of applications. As light emitting materials, the compounds can be useful in organic light emitting diodes (OLEDs), luminescent devices and displays, and other light emitting devices, or as luminescent markers in bio-applications.

The emission (and absorption) profile of the compounds can be tuned by varying the structure of the ligand surrounding the metal center. For example, compounds having a ligand with electron withdrawing substituents will generally exhibit different optical properties, including emission and absorption, than compounds having a ligand with electron donating substituents. Generally, a chemical structural change affects the electronic structure of the compound, which thereby affects the absorption and emission of the compound. Thus, the compounds of the present invention can be tailored or tuned to a specific application that desires a particular emission or absorption characteristic.

In another aspect, the iridium compounds can be used as luminescent markers for bio-applications, emitters for organic light emitting diodes, as catalysts, and as absorbers for organic photovoltaics.

In one aspect, the disclosed compounds comprised of phosphorescent iridium complexes. Through ligand modification, the emission energy and width can be tuned, making the series suitable in electroluminescent devices.

In another aspect, the emission spectrum of any of the compositions of the present disclosure can be tuned to a desired and/or customized spectrum. In another aspect, the complexes disclosed herein can provide a narrow bandwidth, enabling their use in, for example, applications in which broad spectrum emitters are not suitable.

In still another aspect, an expansion utilizing different emitting portions and linking groups should provide narrow emitting complexes covering a wide range of the visible spectrum. The emission energy of a certain complex can be tuned by modifying the ligands disclosed herein. This can be accomplished through changes in structure that modify the energy of the donating or accepting portion of the emitting fragment.

In one aspect, the inventive compositions are useful as emitters for full color display application. In such an aspect, the geometry of cyclometalating ligands can be rigid. This rigidity can allow for similar geometry between the ground and excited state, resulting in a narrow emission spectra dominated by the transition from the lowest vibrational level in the excited state to the lowest vibrational level in the ground state.

In a further aspect, the molecular structure having six coordinating ligands to a metal center can be preferred. In such an aspect, a four ligand coordinated structure can at least partially ensure the electrochemical and/or photophysical stability of the complex during, for example, fabrication and operation of a color display device.

In another aspect, the inventive compositions can provide improved efficiency and/or operational lifetimes in lighting devices, such as, for example, organic light emitting devices, such as OLEDs, as compared to conventional materials. Thus, also disclosed herein are devices comprising the complexes described herein. One application for phosphorescent emissive complexes, such as those described herein, is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

In other various aspects, the inventive compositions can be useful as, for example, luminescent labels, and emitters for organic light emitting diodes, lighting applications, and combinations thereof.

The compounds of the invention can be made using a variety of methods, including, but not limited to those recited in the examples provided herein. In other aspects, one skilled in the art, in possession of this disclosure, could readily determine an appropriate method for the preparation of an iridium complex as recited herein.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Synthesis of Iridium Compounds

The general synthesis of the disclosed compounds is shown below.

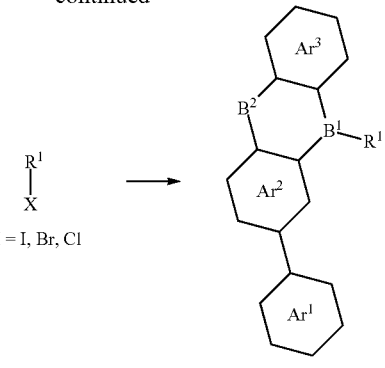

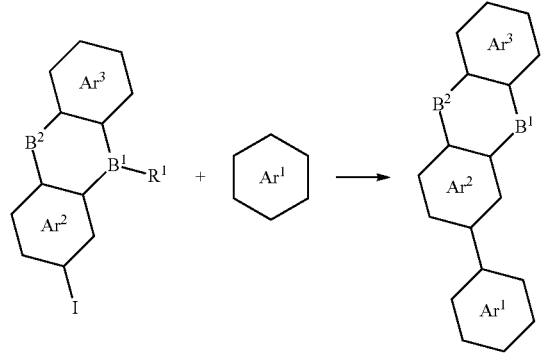

In a non-limiting example, the scheme below shows the synthesis of a carbazole iridium compound.

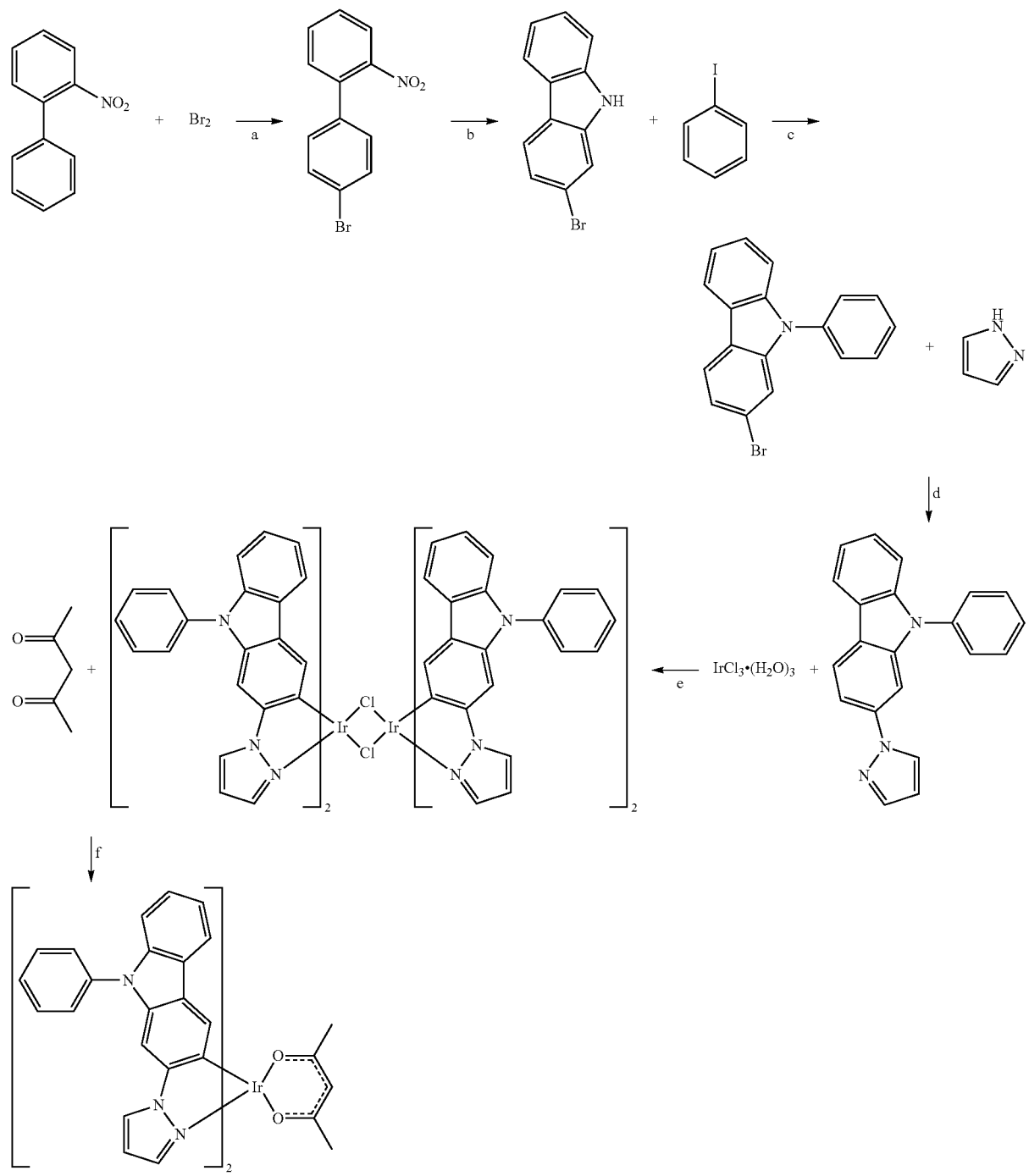

Step (a). A three neck flask was charged with 2-nitrobiphenyl (1 mol), iron trichloride (55 mmol), and water (200 mL) and set to stir under a nitrogen atmosphere for 30 minutes. Bromine (1.25 mol) was added dropwise over the course of one hour, then set to reflux for four hours, cooled to 60° C., and stirred for 12 hours. Sodium bisulfate (500 mmol) was added slowly, and the mixture rinsed three times with water (200 mL), twice with 5% sodium hydroxide solution (100 ml) and twice more with water (200 mL). The solids were dissolved in dichloromethane, dried over magnesium sulfate, and flashed chromatographed over silica with dichloromethane as the eluent. The solvent was removed under reduced pressure and the crude product recrystallized from ethanol to give 4'-bromo-2-nitrobiphenyl in 35% yield.

Step (b). Around bottom flask was charged with 4'-bromo-2-nitrobiphenyl (100 mmol) and triethyl phosphite (100 mL) and set to reflux under a nitrogen atmosphere for 24 hours. Upon cooling, the solvent was distilled off under vacuum, and the crude product was recrystallized from hot toluene to give 2-bromo-9H-carbazole in 40% yield.

Step (c). A pressure vessel was charged with -bromo-9H-carbazole (10 mmol), iodobenzene (20 mmol), potassium carbonate (20 mmol), L-proline (2 mmol), copper(I) iodide (1 mmol), and dimethyl sulfoxide (25 mL). After three cycles of evacuation and backfilling with nitrogen, the vessel was sealed and stirred at 90° C. for three days. After cooling, the reaction mixture was diluted with dichloromethane (200 mL), washed four times with water (200 mL), and dried over magnesium sulfate. After removing the solvent under reduced pressure, the crude product was chromatographed over silica with hexane as the eluent, giving 2-bromo-9-phenyl-9H-carbazole in 85% yield.

Step (d). A pressure vessel was charged with 2-bromo-9-phenyl-9H-carbazole (10 mmol), pyrazole (20 mmol), potassium carbonate (20 mmol), L-proline (2 mmol), copper(I) iodide (1 mmol), and dimethyl sulfoxide (25 mL). After three cycles of evacuation and backfilling with nitrogen, the vessel was sealed and stirred at 90° C. for three days. After cooling, the reaction mixture was diluted with dichloromethane (200 mL), washed four times with water (200 mL), and dried over magnesium sulfate. After removing the solvent under reduced pressure, the crude product was chromatographed over silica with hexane as the eluent, giving 9-phenyl-2-(1H-pyrazol-1-yl)-9H-carbazole in 45% yield.

Step (e). A round bottom flask was charged with 9-phenyl-2-(1H-pyrazol-1-yl)-9H-carbazole (2 mmol), iridium chloride trihydrate (1 mmol), and 2-ethoxyethanol (25 mL) and set to stir at reflux under a nitrogen atmosphere for 24 hours. After cooling, the solvent was removed under reduced pressure and the solids rinsed with diethyl ether. The chloride bridged iridium dimer was used in the subsequent reaction without further purification.

Step (f). A round bottom flask containing the chloride bridged iridium dimer was charged with acetylacetone (3 mmol), potassium carbonate (5 mmol), and 1,2-dichloroethane and set to stir at reflux under a nitrogen atmosphere for 24 hours. After cooling, the reaction mixture was diluted with dichloromethane (100 mL), washed three times with water (100 mL), dried over magnesium sulfate, and the solvent removed under reduced pressure. The crude product was chromatographed over silica with dichloromethane as the eluent, giving the example iridium complex in 75% yield.

Properties of Carbazole Iridium Compounds

The emission specta of the compound below is shown in FIG. 1.

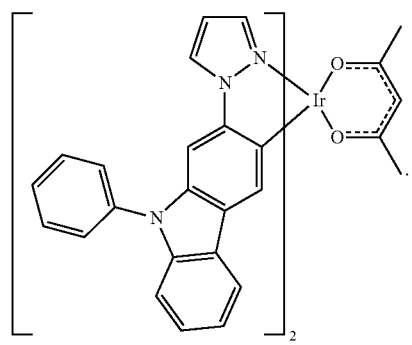

What is claimed is:
1. A compound having the structure:

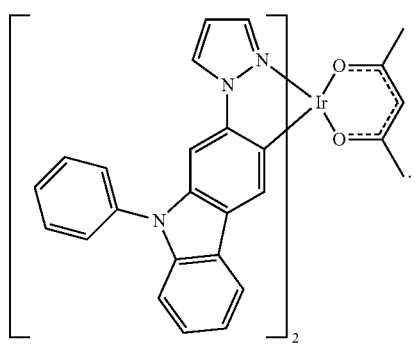

2. A electroluminescent device comprising the compound of claim 1.
3. An organic light-emitting diode (OLED) comprising the compound of claim 1.
4. An organic photovoltaic device comprising the compound of claim 1.

* * * * *